United States Patent
Wohltjen

(10) Patent No.: US 8,279,063 B2
(45) Date of Patent: Oct. 2, 2012

(54) PERSONNEL LOCATION AND MONITORING SYSTEM AND METHOD FOR ENCLOSED FACILITIES

(75) Inventor: Henry Wohltjen, Bowling Green, KY (US)

(73) Assignee: Xhale, Inc., Gainesville, FL (US)

( * ) Notice: Subject to any disclaimer, the term of this patent is extended or adjusted under 35 U.S.C. 154(b) by 640 days.

(21) Appl. No.: 12/269,595

(22) Filed: Nov. 12, 2008

(65) Prior Publication Data

US 2010/0117823 A1    May 13, 2010

(51) Int. Cl.
*G08B 1/08*    (2006.01)
(52) U.S. Cl. .................. 340/539.13; 340/573.1
(58) Field of Classification Search ........... 340/539.13, 340/539.11, 573.1, 539.1, 539.12
See application file for complete search history.

(56) References Cited

U.S. PATENT DOCUMENTS

| | | |
|---|---|---|
| 3,566,348 A | 2/1971 | Leyden et al. |
| 4,207,571 A | 6/1980 | Passey |
| 4,751,689 A | 6/1988 | Kobayashi |
| 4,813,025 A | 3/1989 | Rowland et al. |
| 4,938,928 A | 7/1990 | Koda et al. |
| 4,992,244 A | 2/1991 | Grate |
| 5,034,192 A | 7/1991 | Wrighton et al. |
| 5,071,770 A | 12/1991 | Kolessar, Jr. |
| 5,145,645 A | 9/1992 | Zakin et al. |
| 5,252,292 A | 10/1993 | Hirata et al. |
| 5,337,018 A | 8/1994 | Yamagishi |
| 5,528,232 A | 6/1996 | Verma et al. |
| 5,605,612 A | 2/1997 | Park et al. |
| 5,756,879 A | 5/1998 | Yamagishi et al. |
| 5,783,154 A | 7/1998 | Althainz et al. |
| 5,830,412 A | 11/1998 | Kimura et al. |
| 5,918,257 A | 6/1999 | Misfund et al. |
| 5,945,069 A | 8/1999 | Buehler |
| 6,404,703 B1 | 6/2002 | Burrell |
| 6,426,701 B1 | 7/2002 | Levy et al. |
| 7,010,290 B2 | 3/2006 | Dent |

(Continued)

FOREIGN PATENT DOCUMENTS

WO    WO2007/090470    8/2007

(Continued)

OTHER PUBLICATIONS

Chung, Wan-Young, et al., Passive and Cost Effective People Indoor Location Tracking System for Ubiquitous Healthcare. 6th Iasted International Multi-Conference on Wireless.

(Continued)

*Primary Examiner* — Daniel Previl
(74) *Attorney, Agent, or Firm* — Gerard H. Bencen

(57) ABSTRACT

A wireless time-of-flight distance measurement device and/or a motion detector is used at each of a plurality of stations in a wireless network in an enclosed facility to accurately locate a badge-wearing person near the station. The location, badge number and time of detection are transmitted through the network and stored in a computer memory. In a health care facility, hand-washing detectors are located at some of the stations and caused to energize a hand-wash status indicator light on the badge when the wearer has washed his or her hands. The light remains "on" for only a certain length of time, but will be extinguished sooner by a monitor device near each patient when the health care worker leaves the vicinity of the patient. These events also are transmitted and stored so that a timed record of each worker's hand-washing and visits to patients is created.

35 Claims, 4 Drawing Sheets

U.S. PATENT DOCUMENTS

| | | | |
|---|---|---|---|
| 7,015,816 B2 | 3/2006 | Wildman et al. | |
| 7,031,224 B2 | 4/2006 | Reifer | |
| 7,148,803 B2 | 12/2006 | Bandy et al. | |
| 7,171,312 B2 | 1/2007 | Steinthal et al. | |
| 7,242,307 B1 | 7/2007 | LeBlond et al. | |
| 7,293,645 B2* | 11/2007 | Harper et al. | 206/205 |
| 7,363,125 B2 | 4/2008 | Hasimoto et al. | |
| 7,408,470 B2* | 8/2008 | Wildman et al. | 340/573.1 |
| 7,408,839 B2* | 8/2008 | McFarland | 367/124 |
| 7,755,494 B2 | 7/2010 | Melker et al. | |
| 7,818,083 B2* | 10/2010 | Glenn et al. | 700/108 |
| 7,898,407 B2* | 3/2011 | Hufton et al. | 340/539.11 |
| 2002/0067660 A1 | 6/2002 | Bokhour | |
| 2006/0074494 A1 | 4/2006 | McFarland | |
| 2007/0205886 A1* | 9/2007 | Huseth et al. | 340/539.15 |
| 2007/0247316 A1 | 10/2007 | Wildman et al. | |
| 2008/0103636 A1 | 5/2008 | Glenn et al. | |
| 2009/0051545 A1* | 2/2009 | Koblasz | 340/573.1 |

FOREIGN PATENT DOCUMENTS

| | | |
|---|---|---|
| WO | WO2008/088424 | 7/2008 |

OTHER PUBLICATIONS

Sensor Networks, Jul. 3-2, 2006, BANFF, AB, Canada, pp. 527-530.

Priyantha, N.B, et al, The Cricket Location-Support System, 6th ACM International Conference on Mobile Computing and Networks, Boston, MA, Aug. 2000, 12 pages.

* cited by examiner

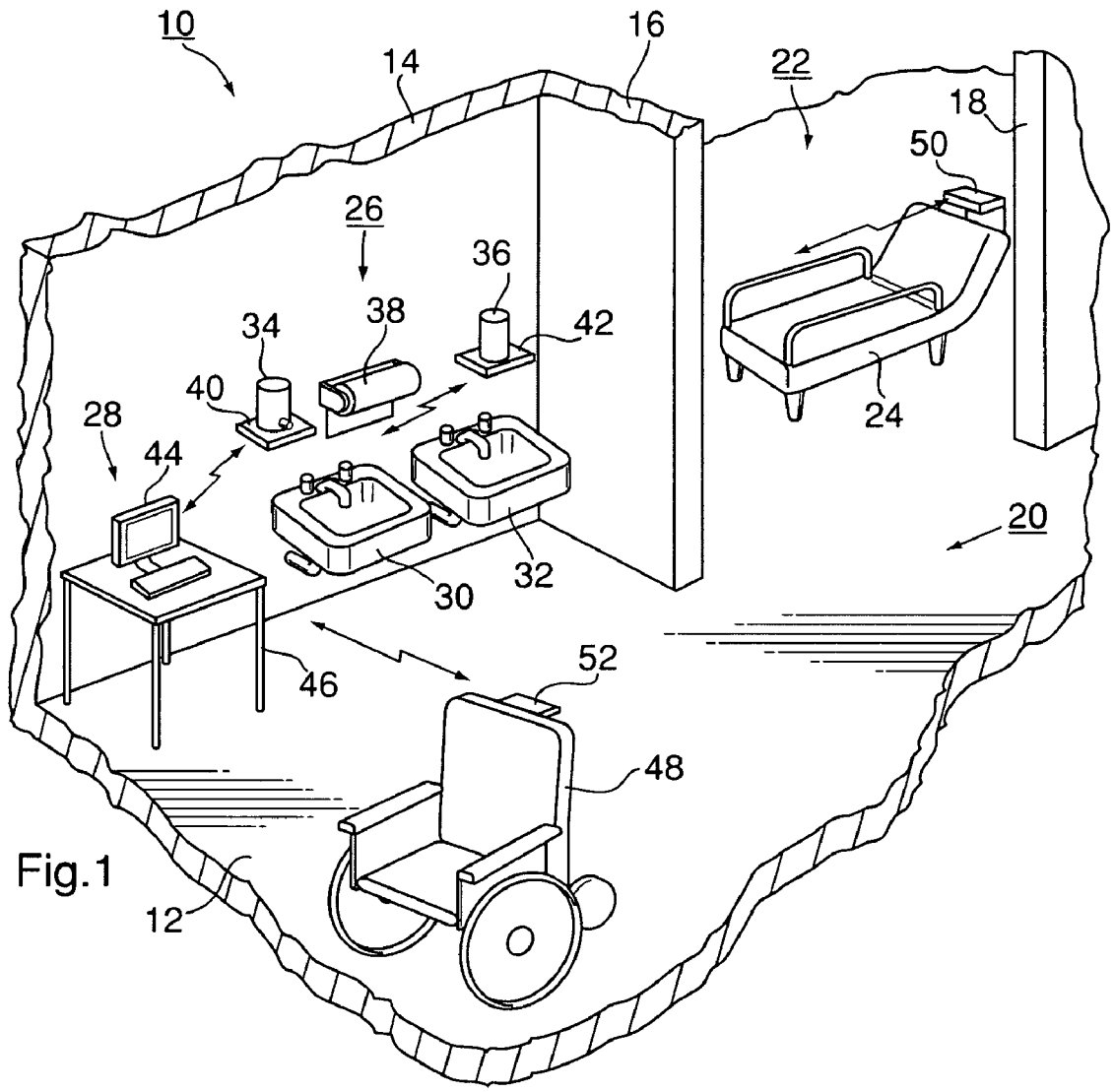
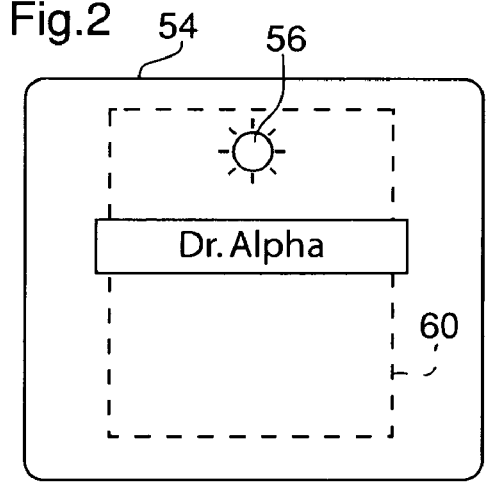
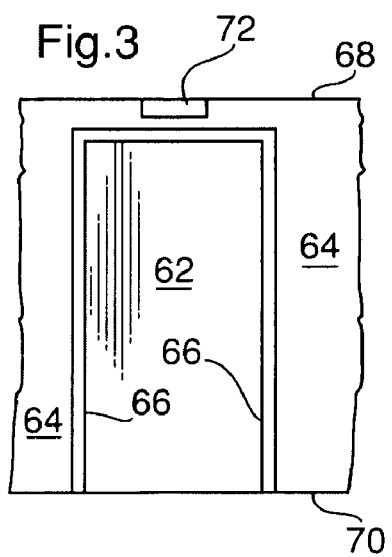

PERSONNEL LOCATION AND MONITORING SYSTEM AND METHOD FOR ENCLOSED FACILITIES

This invention relates to the location and monitoring of personnel in an enclosed facility. The invention also relates to the monitoring and control of hand-washing by personnel in health care facilities and the like.

In many enclosed facilities, it is highly desirable or necessary to locate the positions of various personnel in the facility at various times of the day. This can be useful or necessary for purposes of monitoring the movement of people in secure facilities to make certain that they are not moving into or out of areas without authorization, to provide a record of movement by health care workers in hospitals, clinics and the like, and to determine when each person enters or leaves the facility.

In particular, in hospitals, it is highly desirable to have a stored record of the location of each health care worker in the hospital throughout the working day. This can provide valuable records tending to prove health care treatment of specific patients at specific times, and other valuable information.

It also is desired to detect and record information indicating the hand-wash status of each health-care worker at any time during a work day, as well as the location of the worker when the hand-wash status is determined.

An object of the invention is to provide a stored record of the hand-washing activities of each worker in a health care facility over a given period of time, to assist in the encouragement of the health care workers to wash their hands as frequently as necessary to minimize the spread of infections to patients within the facilities, and to provide records establishing the degree of compliance of each health care worker with regulations governing such activities.

The invention can be used in various facilities such as, patient care facilities, such as nursing homes, clinics, rehabilitation centers, doctors and dental offices, etc. medical laboratories, clean-room manufacturing facilities, and facilities otherwise requiring frequent hand-washing to retard the distribution of pathogens. Examples of the latter include restaurants, food processing facilities such as slaughter houses, egg and meat packing plants, fresh fruit and vegetable packaging plants, institutional kitchens, etc.

The need for regular, frequent hand-washing in health care facilities is very important. It has been established that the failure of medical personnel to wash their hands frequently enough annually leads to many infections of patients in the facilities with diseases that they did not have previously. Annually, this causes deaths of the patients and many serious new infections requiring substantial time and expense and suffering by the patients to cure.

The cost to the hospitals is very large. Insurance providers often refuse to compensate the hospital for any expenses caused by such infections so that the hospitals suffer severe financial losses from their occurrence.

As a result, stringent hand-washing regulations have been enacted by government regulators. These regulations specify, for example, that the hands must be washed both before and after contact with each patient.

Although health care workers, including doctors, nurses and other personnel, have been warned and instructed in the requirements for hand-washing, the degree of compliance often is mediocre to poor. As a result, related infection rates in hospitals and other health care facilities often are unacceptably high.

Various systems and methods have been proposed in the past for preparing hand-wash status records of medical personnel in hospitals and other health care facilities. In such proposals, RF or other signaling is used in connection with badges worn by health care personnel. However, such prior systems are believed to be deficient and are not believed to be in widespread use.

Another problem in health care facilities is the monitoring of the visits of the personnel to specific patients, and the hand-wash status of such personnel. Records of such visits and the hand-wash status of the visitors would tend to substantiate the level of care and the hand-cleanliness of caregivers for the patient at any given time. Such records would be useful in determining insurance claims and in regulatory inquiries.

A further problem is that the accuracy and reliability of the hand-wash status indicators worn by health care personnel need improvement so that the need for washing the hands is indicated reliably and can be used by the health care personnel themselves, as well as patients and others, to reliably indicate the need for the hands to be washed.

Another problem with which this invention is concerned is the location of patients who are moved from their beds to another location in the health care facility, and the monitoring of caregiver contact with those patients.

Accordingly, it is an object of the present invention to provide an accurate and reliable enclosed facility personnel location system and method, and a health care facility personnel location and hand-washing monitoring system and method which alleviates or corrects the above described problems.

Specifically, it is an object to provide a wireless system and method which is relatively error-free in detecting the whereabouts of personnel, and hand-wash status of medical personnel, in an enclosed facility.

It is another object of the invention to provide such a system and method which detects and records when each health care worker washes his or her hands, when each such worker comes in close proximity to a patient, and gives to all an indication of the hand-wash status of the worker.

It is another object of the invention to provide a system which records such information automatically as the personnel and patients move within the facility, and provides a stored record which is retrievable and from which compliance records can be prepared, for use in proof of compliance and treatment visits to patients, and other relevant information for such personnel.

It is a further object to provide such systems and methods which are wireless, relatively simple and low cost, reliable in operation, have very low power requirements and long battery life, and require relatively low maintenance and are largely trouble-free.

In accordance with the present invention, the foregoing objects are met by the provision of a system and method for locating personnel in an enclosed facility having a plurality of spaced-apart stations, in which an indicator tag or badge is carried by each of the personnel.

Equipment is provided at each station to determine when each tag is within a predetermined distance from the station, and to record the number of the tag and time of the event.

This is done, preferably, by transmitting first and second wireless signals between the station and the tag. The signals have significantly different transmission velocities. One signal preferably is an RF signal, and the other is ultrasonic. The difference in the transmission times of the signals is measured, and when that difference is below a predetermined level, the location and tag number are recorded by sending the information through a network to storage, where it is stored together with the time and date on which the record is stored.

In accordance with another feature of the invention, the various stations within the facility are associated with one another in a wireless network e.g. a "ZigBee" network, which is very simple and inexpensive to build and maintain. Preferably the data is encrypted for secure transmission. Thus, there is created a usable record for all of the personnel present in the facility over a given time period.

Other relatively simple wireless local area networks such as Wi-Fi, Bluetooth, etc. can be used instead, if desired or needed.

When used in a health care facility, such as a hospital, each identification tag or badge is worn by an individual associated with and whose name appears on that tag. The tag also bears means such as a visible LED for indicating to all the hand-wash status of the wearer, and, optionally another indicator such as a vibrator to tell the wearer that hand washing is needed.

In at least some of the stations within the facility, hand-washing equipment is provided, in addition to the distance detection equipment described above. At each such hand-wash station, a hand-wash detector is provided to detect and indicate the satisfactory completion of a hand-washing operation by the badge-wearer and to transmit this information to the badge and turn on the LED. The LED remains lighted for a pre-determined time, during which it is discernable by all to indicate the hand-wash status of the wearer.

The hand-wash detector preferably senses the vapors emanating from the hands of an individual immediately after he or she has washed the hands with a substance containing a chemical taggant, such as alcohol, which also is a bactericide. However, other hand-washing detectors which are known in the art can be used instead, if desired.

In accordance with another feature of the invention, location detectors, preferably of the same general type as those used at the hand-wash stations are mounted near or onto a patient beds, and on wheelchairs, gurneys, and other internal hospital transportation and/or patient-supporting devices for detecting the tag of each person who approaches the patient close enough to touch the patient or otherwise transmit pathogens to the patient.

These monitors are referred to herein as "bed monitors" or "transportation monitors", respectively.

Thus, when a health care worker approaches to within a predetermined distance of a patient located in a bed or on another support, the bed or transportation monitor records the identify of each individual tag that is detected, the identity of the patient and the hand-wash status of the worker, and transmits this information through the network, to the data storage facilities, where it is stored together with the date and time of the transmission.

When the patient is transferred from his or her bed to a wheelchair or other conveyance, the information identifying the patient and the bed location stored in the bed monitor is transferred to a similar transportation monitor mounted on the transportation means, which will detect and record close encounters with other personnel.

As noted above, preferably, each badge or identity tag worn by personnel in the hospital facility has an indicator LED, such as a green light, which is lit immediately upon the successful completion of a hand-washing operation. The LED stays lighted for a predetermined length of time, such as ten minutes, at which time the light is extinguished and the wearer must wash his or her hands again in order to relight the LED.

It usually is required that each health care worker wash his or her hands both immediately before and immediately after touching or coming close to any patient. Therefore, an additional advantageous feature of the invention is to provide means in each bed monitor and each transportation monitor to hold the green light on, if it is on when first detected, for as long as the health care worker remains sufficiently close to the patient.

It also is advantageous to automatically turn the light off as soon as the health care worker moves away from that patient to go elsewhere, even if the time set for the light to go out (e.g., 10 minutes) has not expired. This will tend to encourage the health care worker to wash his or her hands before approaching the next patient. This also may comfort the patient who sees the green light.

The use of a single indicator light on the identity tag is not essential to the invention, but is preferred as being potentially more acceptable to both patient and health care worker than one like those proposed in the past, which shows another light (usually red) when the time after the previous hand-washing has expired. Furthermore, the single light limits power usage. Optionally, a vibrator can be used in the tag to remind the worker of the need for hand washing.

It is believed that, if the indicator works accurately, it will allow the patient to reinforce the requirement of hand-washing by the health care worker serving the patient, and also will engender respect for and reliance on the indicator system.

An alternative is to simply leave the green light "on" until the "on" time expires, regardless of where the worker goes. Although this is simpler to do, it is less informative to patients and workers.

An alternative embodiment of the invention uses a monitor detector, either in addition to the distance measurement device, or instead of it, to enable the monitor/personnel locator.

In the bed monitor, the motion detector stops the unit from emitting "pings" unless the motion of a person at the side of a patient support (e.g., bed) is detected. This can help reduce battery drain, and does not depend upon being able to detect a badge within range.

In the hand wash monitor/locator, the motion detector will start the sending of signals to and receiving of signals from the badge, regardless of whether the badge wearer has turned the unit on. Thus, the person has been located, even if he or she does not attempt to wash his or her hands.

The foregoing and other objects and advantages of the invention will be set forth in or apparent from the following description and drawings.

IN THE DRAWINGS

FIG. 1 is a broken-away perspective view, partially schematic, of an enclosed facility such as a hospital together with various components of the locating and detection system of the invention;

FIG. 2 is a front elevation view of a one embodiment of an identity tag worn by personnel in the facility shown in FIG. 1;

FIG. 3 is a schematic diagram illustrating the use of a monitor at a doorway to detect and record the passage of a person through the doorway;

GENERAL DESCRIPTION

Figure 4:
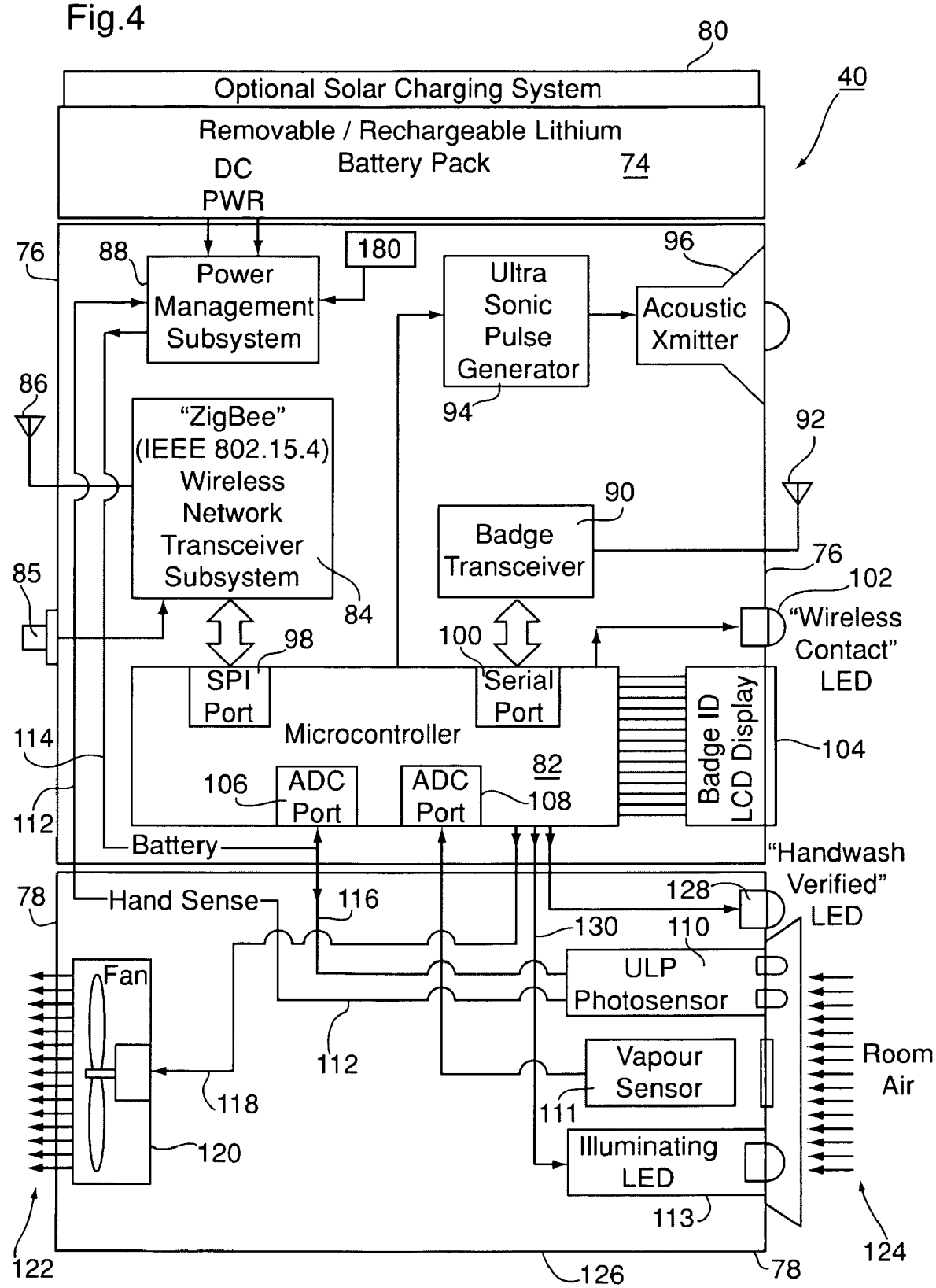
FIG. 4 is schematic block diagram of a location unit and a hand-wash detector/verification unit constructed in accordance with one embodiment of the invention.

FIG. 1 shows a broken-away portion 10 of enclosed facility, in this case a hospital, in a preferred embodiment of the invention.

The hospital is a typical enclosed facility having several stories, each having a floor 12, vertical walls 14, 16 and 18 forming a hallway 20, and a patient room 22 containing a patient bed 24.

In the hallway 20 is a hand-washing station 26 and a personal computer 44 at a station 28, with the computer 44 sitting on a table 46, for use in a network or otherwise as described below.

At the hand-washing station 26 are two sinks 30 and 32, two dispensers 34 and 36 of bactericidal soap for use in washing the hands, and a towel dispenser 38. A personnel locator and hand-wash detector 40 or 42 is located closely adjacent each dispenser 34 or 36.

The term "hand-washing station", as used herein includes not only stations like station 26 shown in FIG. 1, but also other stations which consist of nothing more than a wall-mounted dispenser of alcohol-containing gel or liquid, such as dispensers sold under the "Purell" trademark. Such dispensers already are used in this way in many hospitals today. There need not be a wash basin at the site, as long as a suitable hand cleaner dispenser is available there.

Mounted on or near the patient bed 24 is a personnel locator or "bed monitor" 50. In the hallway is a wheel chair 48 for transporting patients. The wheel chair 48 is representative of gurneys and other such transportation devices as well. The wheel chair 48 has attached to it a personnel locator or "transportation monitor" 52, which is basically the same as the bed monitor 50.

The bed 24, the wheelchair 48, and tables all are referred to herein as "patient support"-structures on which a patient may sit or lay down.

The term "transportation monitor" includes monitors for use in transporting patients both inside and outside of the hospital enclosure, such as in ambulances (ground or airborne), etc.

The bed monitors need not be mounted on the bed or other patient-supporting surface, and might be mounted to advantage on the ceiling above a bed, or on a wall near the bed, or wherever it best detects identity tags reliably.

FIG. 2 shows an identity tag or badge 54 which is worn, preferably, by every worker in the hospital, or at least by all of those who will or might come in close proximity to patients in the hospital.

The tag 54 includes an indicator light 56, preferably a green LED, which is visible to others, as well as the wearer, to indicate the hand-wash status of the wearer. In the area 58 is a prominent display of the name of the health care worker to whom the tag is assigned.

Figure 5:
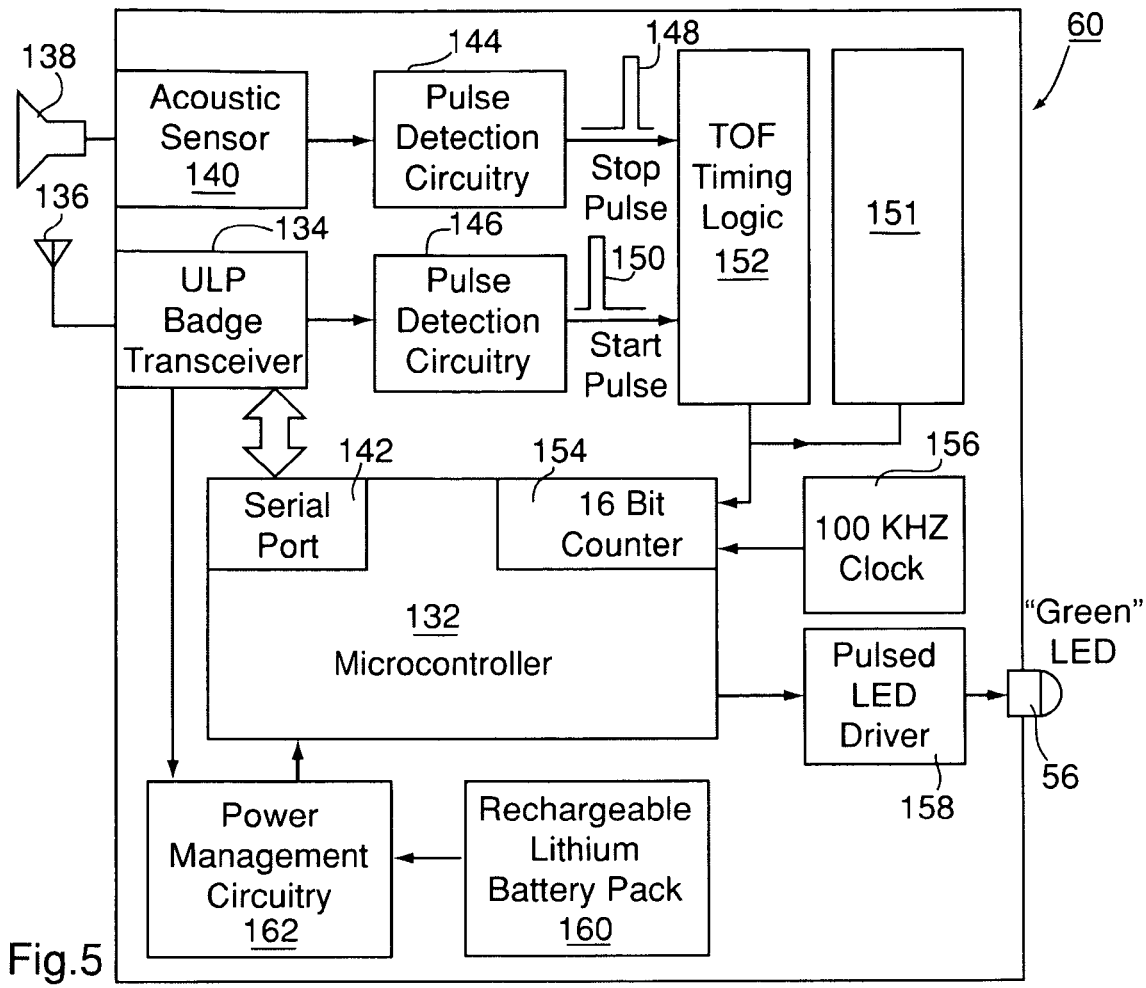
FIG. 5 is a schematic block diagram of the electrical components of the identity tag shown in FIG. 2.

The dashed line 60 in FIG. 2 schematically represents electronic circuitry and devices shown in FIG. 5 which are located in the tag.

FIG. 3 is an elevation view showing the location of a monitor 72 like the bed monitor 50 on the ceiling 68 near a doorway 62 in a wall 64 with door framing 66 and the floor indicated at 70. The monitor 72 detects the identity tag 54 worn by each person passing through the doorway, and causes that number and hand-wash status to be transmitted through the network and stored.

The network preferably is an ultra-low power wireless network such as a "ZigBee" network which delivers information through a gateway to the central computer system of the hospital or to another data storage device, as it will be described in detail below.

As noted above, other known networks also can be used satisfactorily to implement the invention.

Personnel Locator

FIG. 4 is a schematic diagram showing the electrical and electro-mechanical components of personnel locator and the hand-wash detector unit 40. Each unit 40 includes three separate modules; a removable and rechargeable battery pack 74, such as a lithium battery pack to provide electrical power; a personnel location unit 76, and a hand-wash detection unit 78.

DC power is delivered from the battery pack 74 to the personnel location unit 76. Alternatively, if an electrical outlet is at hand, power can be supplied from an ordinary 120 volt AC outlet and an AC/DC adapter. Then the battery serves as a back-up in case of power failure.

An optional solar charging system 80 can be provided. The unit 80 is well-known; it uses the over-head electrical lighting and photovoltaic cells to recharge the battery pack and thus minimizes or eliminates the chore of recharging the batteries.

The personnel locator unit 76 has a microcontroller 82, which includes a CPU, RAM, ROM, etc. and which is programmed so as to perform the functions to be described below.

Although many suitable microcontrollers are available, one such unit is sold by Silicon Laboratories, Inc. Austin, Tex., Part No. C8051F9XX.

The locator unit 76 also includes a conventional network transceiver unit 84 with an antenna 86 for transmitting and receiving RF signals using the IEEE 802.15.4 protocol used by a ZigBee network. The transceiver 84 is connected to the microcontroller 82 through a SPI port 98.

A second transceiver 90 also is provided and connected to the microcontroller 82 through a serial port 100 to send and receive RF signals through an antenna 92 to and from the badges or tags 56 worn by the personnel. The first RD signal sent preferably contains a unique signal identifying the station which it is issued.

Also provided is an ultrasonic pulse generator 94 which sends ultrasonic pulses through an acoustic transmitter 96 to be received by receiving equipment in the tag or badge 54. The ultrasonic generator for example, a transducer made by Kobitone Audio Company, P/N 255-400SST12ROX, generates pulses at a frequency of approximately 40,000 Hertz. However, other frequencies and other transducers can be used instead.

A LED 102, preferably colored, is provided to be lit whenever wireless contact has been made with a badge that is within range, that is, one which is within a predetermined distance from the unit 76.

A LCD display 104 is provided in order to display the identifying number assigned to the particular tag or badge which has come into range.

A power management subsystem 88 is provided which receives power from the battery pack 74 and delivers a sample of the battery voltage to the microcontroller through an ADC port 106, for the purpose of detecting low battery conditions.

The subsystem 88 also receives a "hand sense" signal over line 112 from an ultra low-power photo detector 110 which serves to turn on the personnel locator 76 and the hand-wash detector 78.

Hand-Wash Detector

The hand-wash detector unit 78 utilizes some of the basic principles of hand-wash detection disclosed in U.S. patent application Ser. No. 11/760,100, filed Jun. 8, 2007 and entitled "Hand-washing Compliance Detection System". The disclosure of that patent application hereby is incorporated herein by reference.

Basically, the unit 78 operates to detect the vapors emanating from a person's hands immediately after the person has washed his or her hands with a cleaning substance including a "taggant" or "marker" material such as alcohol, which is a common bactericidal constituent of hand cleaning materials used in hospitals. The cleaning materials include, for example, alcohol-based hand cleaners; antimicrobial soaps; antiseptic hand-washes; antiseptic hand rubs; detergents; soaps; waterless antiseptic agents; and surgical hand scrubs.

After the person has washed his or her hands using alcohol-containing soap or other materials, dispersed from the dispenser 34 or 36, the person presents his or her hands close to the photosensor 110. This photosensor 110 receives battery power over a line 116 and sends a signal over a line 112 to the power management subsystem 88 that turns on the other subsystems. The microcontroller 82 turns on a small fan 120 through a signal received over a line 118, and energizes a vapor sensor 111 which is specifically selected to sense the vapor emanating from the hands of the user.

The activation of the photosensor 110 starts the operation of the personnel locator 76, as it will be described in greater detail below.

Also, an illuminating LED 113 is lit to provide preferably white light to illuminate the hands of the person presenting them.

The components shown in FIG. 4 are housed in a housing 126. The fan 122 pulls air out of the housing 126 and ejects it in the direction indicated by arrows 122, and draws in room air, including alcohol vapor from the hands of the user, in the direction indicated by arrows 124 to be sensed by the vapor sensor 111.

After a short period of time, when the vapor sensor detects the alcohol vapor, it sends a signal to the microcontroller 82 through an ADC port 108. This causes the badge transceiver 90 to send an RF signal to the badge to light the green indicator light 56. Also, a LED 128 visible from outside of the unit 78 lights to verify that a proper hand-washing operation has been detected.

The vapor sensor ill can be any of a wide variety of known chemical detectors, such as those described in the above-identified co-pending U.S. patent application. However, for the purpose of the present invention, is preferred to use an alcohol detector which is readily available and relatively inexpensive, such as the Model SB30 MOS Heat-Activated Chemical Resistor made by FIS, Inc. of Markham, Ontario Canada. These detectors are widely used in breathalyzers which are used to detect the concentration of alcohol in a person's breath. Of course, other alcohol detectors can be used instead, as desired.

Badge Electronics

FIG. 5 shows the electronic circuit 60 contained in each of the badges or identity tags 54 shown in FIG. 2.

At the heart of the circuit 60 is a microcontroller 132, which can be the same microcontroller as used in the unit 40 shown in FIG. 4.

The circuit 60 also includes power management circuitry 152 and a rechargeable lithium battery pack 160. Terminals on the badge (not shown) are provided in order to recharge the batteries in the tag.

Also provided is an ultra-low power badge transceiver 134, which is a RF transceiver that communicates with the locator unit 76 by means of an antenna 136 to receive RF ranging signals from the unit 76.

Also provided is an ultrasonic receiving unit or microphone 138 and sensor circuit 140 for receiving ultrasonic ranging signals sent from the unit 76. The microphone 138 is, for example, the Part Number SPM020LUDS microphone made by Knowles Electronics, Inc., Itasca, Ill., U.S.A.

Each of the units 134, 140 delivers its output to a pulse detection circuit 146 or 144 which develops a corresponding output pulse. The output pulse of the acoustic circuit is shown at 148 and is called a "stop pulse", and the pulse produced by the RF receiver is indicated at 150 and is called a "start pulse".

An optional vibrator 151, of the type used in cell-phones or the like, is connected for use, under certain circumstances, in warning the wearer that the hand-wash status light 56 is "off", and hand-washing is needed.

Distance Measurement

Pulses 148 and 150 are derived from the corresponding ultrasonic and RF ranging signals received from the locator unit 76. The two signals have vastly different transmission velocities. The RF signals travel at a very high velocity, approaching the speed of light, whereas the ultrasonic signals travel at the speed of sound in air, which is a much, much lower velocity. The pulses 148 and 150 are delivered sequentially to a time-of-flight ("TOF") timing logic circuit 152 which delivers an output signal to a 16-bit counter 154 formed in the microcontroller 132. A clock signal of 100 KHZ is delivered to the counter by a clock circuit 156.

The timing logic circuit 152 is set to determine the number of clock pulses between the start pulse 150 and the stop pulse 148. When that count is less than a predetermined number which indicates a predetermined distance of the badge from the unit 76, an RF signal containing the ID of the badge 54 is delivered by the transceiver 134 through the antenna 136 to the unit 76 (FIG. 4). The unit 76 then transmits a signal to the badge circuit 60 to light the LED 102 to acknowledge that the badge is within range and that a hand wash has been verified upon sensor 11.

This range can be varied as desired, but for the hand-wash unit locators such as the one shown in unit 40, the range can be set at a relatively short distance such as two and a half feet (0.8 meter) so as to prevent the unwanted detection of other badges that might be farther away.

By locating each of the units 40 and 42 near a separate one of the two sinks, and separating the two units 40 and 42 relatively far from one another, there is reasonable assurance that no more than one person will come close enough at any one time to the locator unit 76 to turn it on. This will largely prevent ambiguous simultaneous double-detections.

If necessary, circuitry can be provided to prevent detection of a second badge before the first one is finished processing, if that is necessary. However, it is envisioned that health care personnel will quickly learn to avoid this without the need for any special circuitry.

Of course, it may be possible to use a single unit for two adjacent sinks, since the unit is turned on by a hand presented to the vapor sensor 11.

Referring again to FIG. 5, as well as FIG. 4, when the vapor sensor 111 has detected a high enough vapor level on the hand of the health care worker, the microcontroller causes the badge transceiver 90 to send an RF signal through the antenna 92 to the transceiver 134 of the badge, which then, by way of the microcontroller 132, energizes a LED driver circuit 158 which lights the green LED 56 so that the badge indicates that the wearer has washed his or her hands within the last several minutes.

The microcontroller 132 contains a timer, formed by software, which maintains energization to the driver circuit 158 to keep the green LED 56 "on" for a predetermined time, such as ten minutes, as explained above. After the time has lapsed, microcontroller 132 extinguishes the green LED 56. The LED 56 remains unlit or "off" until relit by another hand-washing detection.

The microcontroller 132 can be programmed to perform a different timing function such as turning the light 56 out after only a few seconds, rather than 10 minutes, in response to the receipt of different signals, say pulses a few seconds a part, for purposes to be explained below.

The microcontroller 132 also can be programmed to measure a different distance, in response to the receipt of different input signals (e.g. pulses of a few seconds a part) for purposes to be described below.

Data Transfer

The personnel locator, when it has received the return message from the badge and the hand-wash detector has finished its work, sends the following data through the ZigBee network to the hospital computer storage server or another data storage device:
1. The identity of the locator unit.
2. The badge number that has been read.
3. Whether a hand-washing procedure has been performed by the badge wearer.

The data is sent to the storage location together with a time and date stamp which is applied automatically by the storage equipment.

Therefore, there is stored a dated history of hand-washing for each badge wearer. This record can be referred to when proving compliance or non-compliance with hand-washing regulations, etc.

In an alternative embodiment, where it is not desired to immediately store the detection data in the main memory of the hospital computer system, time and date data can be added to each information batch stored in a local computer such as the computer 44 and later down-loaded to the main memory.

In any event, the time and date of each personnel location event is stored in memory, preferably without having to transmit the time and date information in the wireless network so as to minimize the data rate required.

Bed Monitors

Each of the units of the "bed monitor" 50 and "transportation monitor" 52 is structurally and functionally the same as that forming the units 74, 76 and, optionally 80, shown in FIG. 4, with certain modifications.

One modification is that, rather than being dormant until the health care worker energizes a photosensor by presenting his or her hand, the bed monitor repeatedly, at pre-set time intervals, sends out ranging signals or "pings" until it detects a badge which is within range.

The "range" or maximum limit for the distance at which badges are detected usually will be longer than the corresponding distance at hand-wash stations, may be 6 feet to 9 or 10 feet, e.g. (2 to 3 meters).

In addition, it is preferred that the monitor automatically extinguishes the green LED when the caregiver leaves the patient to go elsewhere, and that the monitor holds the green LED "on" for as long as the caregiver remains near the patient.

These features will be described in greater detail below.

When a "ping" is sent out and a badge is detected within range by the monitor, the badge identification number and the condition of the green LED on the badge ("on" or "off") is transmitted through the ZigBee network to the data storage system, where it is time-stamped, dated, and stored.

This procedure is repeated for each other caregiver who approaches the same patient within monitor range. The second or further badges detected with the same "ping" will be ignored and detected by a later "ping".

Also, each of the monitors has its own identification number and that is transmitted and stored in memory as well. The storage system now contains the following information.
1. The badge identification;
2. The time and date of entry;
3. The identification of the station; and
4. The status of the hand-wash LED worn by the caregiver.

Therefore, as with the device 40 at the hand-wash station, the presence or location of the person at a given time and date is recorded, along with that person's hand-wash status when the person arrived at the location.

The presence of a particular caregiver at the bedside of a particular patient at a given time and date can be of substantial value in corroborating disputed claims of treatment given to the patient. The hand-wash status information can corroborate the hygienic standards of the visit, as well as providing data for a compliance profile for the caregiver.

The frequency of transmission of the ranging signals or "pings" can vary from several per second to only one every 15 seconds or more. It is desired to make the frequency as high as possible without creating an excessive power drain on the batteries in the badge. It is believed that a frequency of one pulse every 3 or 4 seconds or less is attainable.

In accordance with another feature of the invention, it is preferred to hold a lighted hand-wash LED 56 "on" while the caregiver wearing the badge is still by the patient's bedside, to prevent possible concern by the patient if the LED goes "off" while the caregiver is at the bedside, and also to turn the LED off automatically whenever the caregiver leaves the bedside to go elsewhere, so as to strongly urge the caregiver to wash his or her hands immediately, before approaching another patient.

These functions can be achieved by proper programming of the microcontroller of the monitor and the badges in a number of ways.

For example, when a badge is first detected by a bed monitor, the monitor sends an identification signal to the badge and the badge stores it. The repetitive pulses sent by the monitor enable the short timing function rather than the long (10 minute) function of the microcontroller. The shorter time is equal, for example, to several "ping" pulses. The new timing cycle is re-started by every successive "ping" received by the badge.

Thus, the badge LED will stay lighted as long as the badge continues to receive one of at least some predetermined number of "pings", and will be automatically extinguished when the "pings" are no longer received due to the caregiver leaving the bedside.

As a precaution against prematurely extinguishing a wearer's green light, the automatic turn-off of the light can be conditioned upon the wearer moving out of range of the monitor, as well as the failure to detect "pings" for an excessive length of time. This will reduce the number of incorrect extinguishment occurrences, if there are any.

When the caregiver proceeds to another patient without first washing the hands, if the indicator light 56 has not been turned "off" already, the badge will receive the identification signal of the new bed monitor, compare it with the one stored with the prior patient, and turn the light off when the two identification signals do not match. Also, in this case, the vibrator 151 can be energized to remind the caregiver to wash the hands.

If the caregiver subsequently washes his or her hands, the LED 56 then will turn "on" again for the full ten minutes, unless another patient is visited sooner.

The "pings" transmitted from personnel locators at handwash stations should differ from those sent by bed or transportation monitors because of the different timing function each would enable. This can be done by varying the pulse rate of the "pings", or the ultrasonic or RF signal frequency, or in other ways within the skill of the art.

The correct conditioning of the green LED 56 on the caregiver's badge can provide a strong inducement towards proper hand-washing.

If the patient can recognize the status, he or she can remind a caregiver whose LED is "off" and insist that the hands be washed. This will give added incentive to the caregiver to wash without being reminded by the patient.

Transportation Monitor

If the patient is transferred from the bed 24 to the wheel chair 48 shown in FIG. 1, the information identifying the patient can be transferred from the bed monitor 50 to the transportation monitor 52 on the wheel chair. This can be done by pressing an exterior button 85 (see FIG. 4) which operates the transceiver 84 so as to transfer the information from the unit 50 to the unit 52.

Subsequently, the unit 52 works in the same way as unit 50 to indicate patient contact by health care workers and cause storage of the badge identities and times. Storage of the monitor number does not, in this case, give location.

When the patient is returned to his or her bed, the information can be transferred from the unit 52 to the unit 50 again. The contact of the patient with specific health care workers at specific times, again is transmitted through the network and stored in computer memory to provide records for the future.

Computer Network

Figure 6:
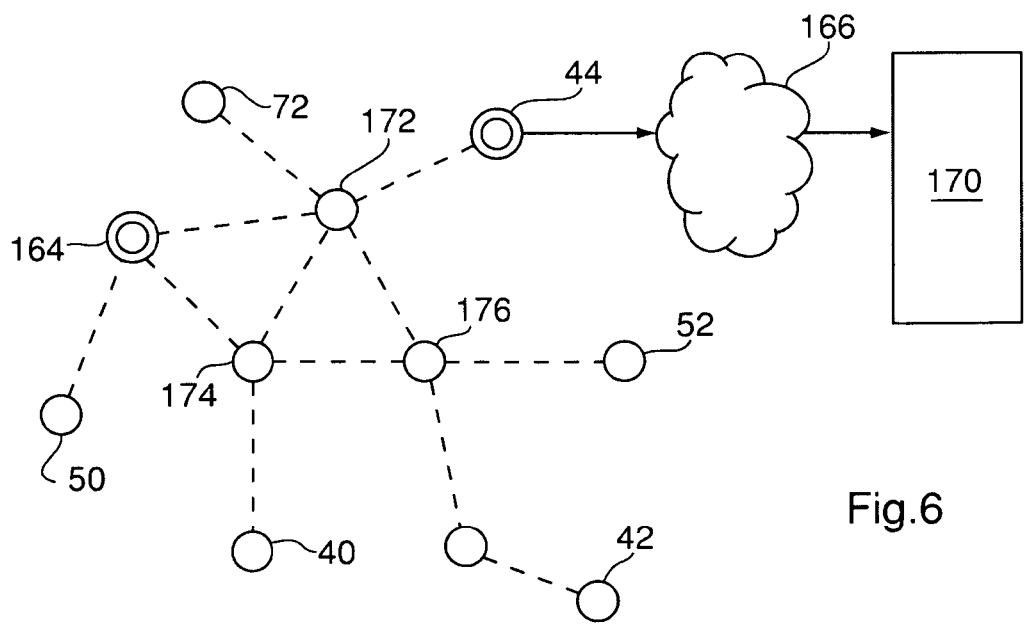
FIG. 6 is a schematic diagram of a network for associating the various monitors and detectors with one another to perform the functions of the invention.
Figure 7:
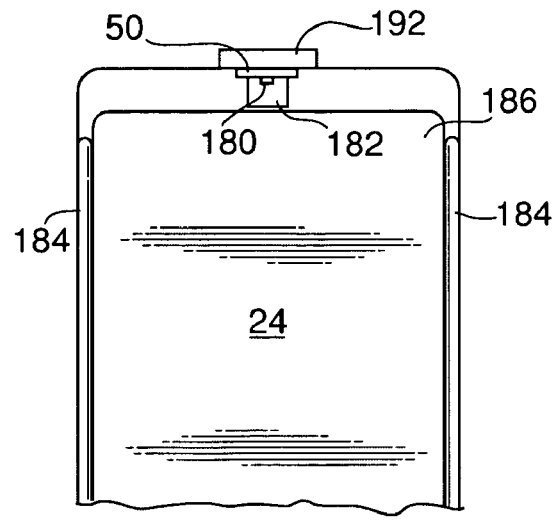
FIG. 7 is a top plan view, partially broken away, of another embodiment of the invention.

The ZigBee computer network used in the invention is shown schematically in FIG. 6 of the drawings. Because a wireless local area network can be extremely variable in configuration, FIG. 6 is only representative of the many different configurations which can exist.

ZigBee network technology is well known and components of the system are standardized. Nonetheless, each separate facility and each separate local area of a large facility may have a different network configuration, depending upon such things as wall locations, equipment locations, etc.

Each network should have a coordinator, one or more routers, and one or more end devices.

In the FIG. 5 network, the network coordinator is indicated at 164. It serves as one "node" of the network. The dashed line between various nodes of the network indicate possible paths of travel of wireless signals.

Routers 172, 174 and 176 are positioned as needed. The coordinator 164 also is a router and the coordinator, together with the units 172, 174 and 176 determines the routing of wireless signals in the network. The end devices in FIG. 6 include the units 40, 42, 50, 52 and 72 which have been described above.

In the network shown in FIG. 6, wireless signals, from the end devices are routed along the best route available, which is determined by software used in the system, and delivered to a gateway device which is, in this case, the PC 44 which also is shown in FIG. 1.

The data is delivered from the PC gateway through the larger network 166 of the hospital or other facility to a bank of servers 170 where the data is stored and from which it can be retrieved to prepare various records for patients and personnel.

As noted above, alternatively, the data can be temporarily stored in the memory of the computer 44 or a connected disk file, and then later downloaded to the server 170. If this is done, the data is automatically timed and date stamped as it is stored in the memory of the computer 44.

The routers 172, 174, and 176 and the coordinator 164 are powered "on" all the time so they can "listen" for communications from the end devices and deliver stored messages, etc. Therefore, these devices should use house current through regular outlets, rather than batteries.

Advantageously, the end devices can be stand-alone battery-operated devices which "sleep" most of the time. This is true for the hand wash detectors and the personnel locators adjacent the hand-washing location.

Examples

Following is an example of a sequence of events which might occur for a given health worker.

First, the worker washes his hands and presents them to a hand-washing detector which lights the green LED on his badge. The LED is set to automatically turn off after a ten minute time delay.

The worker promptly goes to visit a first patient in a bed. When he enters the range of the bed monitor for that bed, the bed monitor detects his badge number and LED condition, and sends that data, together with the bed identification number through the network to the central computer system for storage. The information is time and date-stamped as it passes into the central computer storage system.

The health care worker sits by the bedside of the patient for five minutes and then gets up to leave to visit another patient. After the health care worker's badge has not sensed a "ping" from the bed monitor for a predetermined length of time, the green LED is automatically extinguished even though the ten minute time period originally set for the badge has not yet expired.

Before going to visit the next patient, the health care worker has to again wash his hands and submit them to a hand-wash detector which then relights the green LED, and the health care worker can proceed to visit the next patient.

As another example, assume that the health care worker is finished seeing patients for the time being and takes a lunch break of one half hour. If the green light on the worker's badge was on at the start of the lunch break, it automatically turns off when the ten minute time limit has been exceeded.

Before the worker can resume seeing patients, he must again wash his hands in order to re-light the green LED. This is beneficial because, even though the health care worker has not been visiting other patients, his hands have been exposed to areas and surfaces in the hospital which might bear pathogens, and the hand-washing therefore is beneficial.

The record that is stored and prepared in the central computer system of the hospital will indicate when the last hand-washing occurred before the worker started his lunch break, and will show no patient contact for one half hour while the worker was on lunch break, and then will show the subsequent hand-washing at the end of the lunch break, before the visit to the next patient.

If desired, a bed or transportation monitor can be located in a contaminated area or area which there is extra danger of a caregiver picking up pathogens. The caregiver would be required to wash hands on leaving.

Motion Sensor Embodiments

In further embodiments of the invention, a motion sensor is used at each station in addition to or instead of a distance measuring device. These embodiments are illustrated in FIGS. 4 and 7-10 of the drawings.

Figure 8:
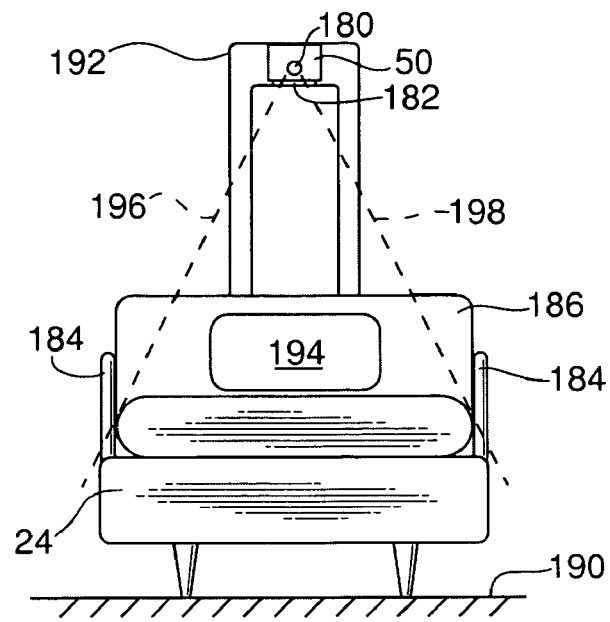
FIG. 8 is a front elevation view of the FIG. 7 embodiment.

The embodiment will be described first as an addition to the bed monitor 50, as shown in FIGS. 7-10. The bed monitor 50 is shown in FIGS. 7-10 mounted on a vertical support frame 192 which extends upwardly from the rear of the bed 24 to a position above the upraised head portion 186 and horizontal portion 188 of the bed. The side rails of the bed are shown at 184, and the bed rests on the floor 190 of a hospital or other health care facility. A pillow 194 is shown in FIG. 8.

Figure 10:
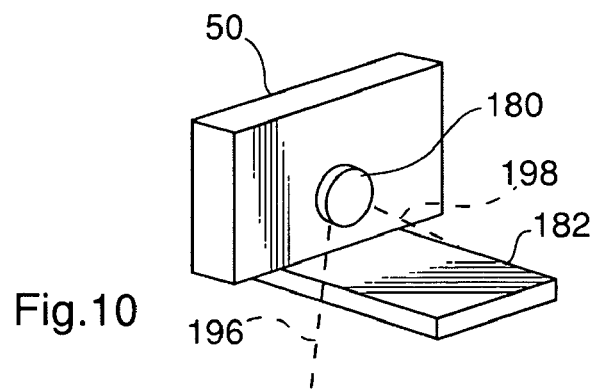
FIG. 10 is a perspective view of a component of the FIG. 7 embodiment.

As it is shown most clearly in FIG. 10, a motion detector sensor 180 is mounted on the outside of the housing of the monitor unit 50. A horizontal plate 182 is attached at a position underneath the sensor 180.

As it is shown in FIG. 8, the plate 182 is dimensioned and shaped so as to form a shield to prevent the sensor 180 from sensing the motion of the patient on the bed, and forming detector area limits 196 and 198 to confine the motion detection function to persons at the sides of the bed 24.

Figure 9:
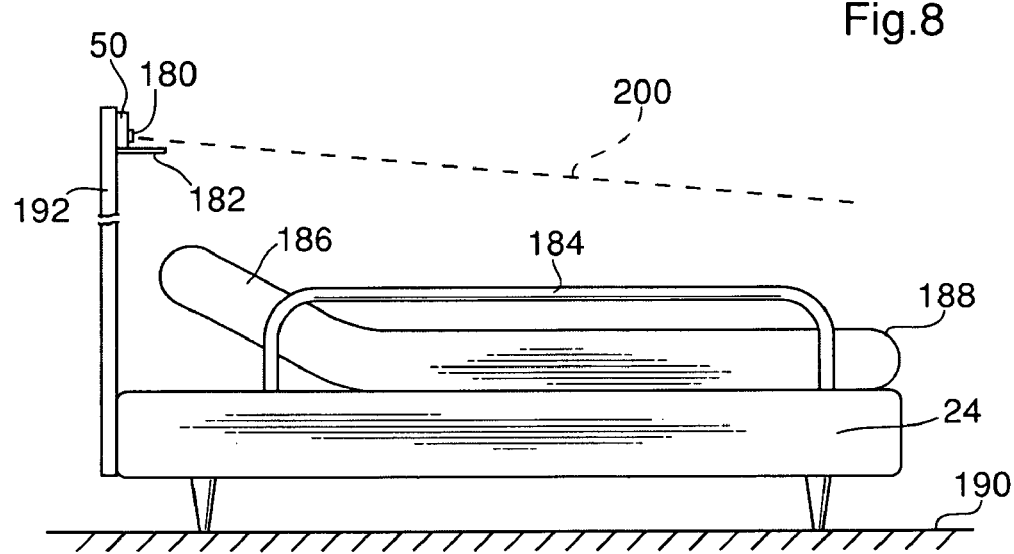
FIG. 9 is a side elevation view of the FIG. 7 embodiment.

Referring to FIG. 9, preferably, the motion detector has a range which does not extend significant beyond the foot of the bed so as to avoid detecting the motion of persons merely passing by.

Referring now to FIG. 4, the motion detector 180 is electrically connected to the power management subsystem 88 to turn on the function of sending sonic signals or "pings" when motion is detected. The microcontroller 82 is programmed to start the sending of pings when it has had no response from a badge for a pre-determined number of pings, and has detected no badge within the range of the distance measurement equipment, and also detects no signal from the motion detector 180.

This function is effective to turn off the pinging function when personnel beside the bed have moved out of range of the monitor unit. This tends to save battery power by preventing the ranging signals from being transmitted when healthcare personnel are not present and moving.

If desired, the motion detector device can be substituted for the distance measuring device of the invention, where it is deemed acceptable despite the lower accuracy in determining the distance of the personnel from the motion detector.

When the motion detector is used in addition to or instead of the distance measurement device at a hand wash station, such as the unit 40 shown in FIG. 4, the unit 76 is turned on by the motion detector instead of the photosensor 110. This means that the badge information and other information are sensed and transmitted at the station through the network for recording, regardless of whether the person attempts to wash his or her hands at the station. This can have the advantage of insuring the location of a given person at a hand wash station at a particular time of day, even though the person does not wash his or her hands.

Although a variety of types of motion sensors can be used, an IR radiometer type such as those widely available from Panasonic and others is believed to be suitable. Although the use of the shield plate 182 is shown, the motion detector sensor itself can be adjusted to exclude the bed 24 from its field of view, if preferred.

If the motion detector is used in addition to the distance measuring equipment, the monitor unit 76 will respond only to the badge which is within the precise distance measurement of the monitor unit, regardless of motion detected beyond that range.

The above description of the invention is intended to be illustrative and not limiting. Various changes or modifications in the embodiments described may occur to those skilled in the art. These can be made without departing from the spirit or scope of the invention.

What is claimed is:

1. A system for locating personnel in an enclosed facility having a plurality of spaced-apart stations, said system comprising:
   (a) a separate indicator badge for each of said personnel;
   (b) at least one detector for detecting when one of said badges is located within a predetermined distance from one of said stations, and for reading information from the detected badge at said station;
   (c) each of said detectors including first and second wireless transmitters for transmitting first and second wireless signals, the signals having transmission velocities different from one another; and
   (d) a device for detecting the difference in transmission times between said first and second signals and indicating when said difference is below a predetermined value.

2. A system as in claim 1 in which said information includes the identity of said badge, said system further comprising equipment for transmitting and storing the identity of said badge, the identity of the station from which said information is transmitted, and the time of such transmission.

3. A system as in claim 1 which said enclosed facility has walls and at least some of said stations are separated from one another by one or more of said walls, said stations being arranged in a wireless network with transceivers for transmitting signals to and receiving signals from one another, and to a storage device.

4. A system as in claim 1 including a hand cleanliness detector at each of a plurality of said stations for detecting and developing a signal indicating the hand cleanliness of the person wearing said badge when it is detected, in which each of said badges has an indicating device for indicating said hand cleanliness, and a wireless signal receiver for receiving said signal from said hand cleanliness detector and enabling said indicating device.

5. A system as in claim 4 in which said indicating device is selected from the group consisting of a visual indicator; a vibrator, and a combination of a vibrator and a visual indicator; and in which each of said badges has a timing device for holding said indicating device in a selected condition for a pre-determined length of time.

6. A system as in claim 4 in which each of said hand cleaning detectors comprises a device for detecting a hand cleaning material on at least one hand of the person wearing said badge and in which said material contains a taggant and each of said cleaning detectors is adapted to detect airborne samples of said taggant.

7. A system as in claim 6 in which said material is selected from the group consisting of alcohol-based hand cleaners; antimicrobial soaps; antiseptic hand washes; antiseptic hand rubs; detergents; soaps; waterless antiseptic agents; and surgical hand scrubs.

8. A system as in claim 1 in which said enclosed facility is selected from the group consisting of a patient care facility, a medical laboratory, a clean-room manufactory, a food processing facility, and a facility otherwise requiring frequent hand washing to retard the distribution of pathogens.

9. A system as in claim 1 in which said facility is a patient care facility having multiple patient care locations and hand washing locations, said stations being located in at least some of said hand wash locations and at least some of said patient care locations.

10. A system according to claim 1 for monitoring hand cleanliness in an enclosed patient care facility having a plurality of spaced apart stations, said system comprising
    (a) an indicator tag worn by each of said personnel;
    (b) a detector at each of said stations for detecting each of said tags when it is located within a predetermined distance from said detector, and for reading information from said tag;
    (c) each of said detectors including first and second wireless transmitters for transmitting first and second wireless signals having different transmission velocities;
    (d) a device for detecting the difference in transmission times between said first and second signals and indicating when said difference is within a predetermined range;
    (e) a hand cleanliness detector at each of said stations for detecting airborne taggant material in hand cleaning material at said station and sending wireless signals responsive to said taggant detection; and
    (f) each of said tags having indicator means for indicating the hand cleanliness of the wearer of said tag, and including a wireless receiver for receiving said wireless signals from said hand cleanliness detector to enable said indicator means.

11. A system as in claim 10 in which one of said transmitters transmits acoustic signals and the other of said transmitters transmits electromagnetic signals.

12. A system according to claim 1 for locating personnel in an enclosed facility having a plurality of spaced-apart stations, wherein said enclosed facility is a healthcare facility comprising;
    (a) a plurality of monitor units, each mounted on or near one of a plurality of patient support structures in said facility;
    (b) a plurality of tags for carrying by personnel present in said facility, each of said tags being responsive to wireless signals from one of said monitor units to transmit identification signals identifying one of said personnel associated with said tag,
    (c) each of said monitor units having equipment for sending ranging signals to said tags,
    (d) a further device responsive to said ranging signals for determining whether the distance of each tag from said monitor unit is within a pre-determined distance; and
    (e) said monitor equipment being adapted to receive said identification signals from one of said tags which is determined to be within said predetermined distance from said monitor unit, and for transmitting a corresponding identification signal to another device for storage together with the time of detection.

13. A system as in claim 12 in which said tag includes an indicator for indicating the hand wash status of the carrier of said tag, and said tag includes a transmitter for transmitting to said monitor a signal indicating said hand wash status, and in which said equipment in said monitor is adapted to transmit a signal corresponding to said hand wash status signal to said other device for storage.

14. A system as in claim 13 in which the indicator included in said tag has an "on" condition to indicate "hands washed" status, includes a holding device for holding said indicator in the "on" condition for a predetermined time after the carrier of said tag has washed his or her hands, and further includes a second holding device responsive to signals from said monitor for holding said indicator in the "on" condition for as long as said tag remains within said predetermined distance from said monitor.

15. A system as in claim 14 in which said monitor is set to repetitively send pulsed signals at regular time intervals, and said second holding device is adapted to start a timing function upon the receipt of each of said pulsed signals and turn said indicator off when said pulsed signals have ceased to be received for a predetermined length of time.

16. A system as in claim 13 including a device for turning said indicator off when the indicator is in a condition indicating "hands washed" status and when said tag has been moved beyond said predetermined distance from said monitor.

17. A system as in claim 16 in which said second holding device is responsive to turn off said indicator, to the simultaneous cessation of receipt of pulsed signals for said predetermined length of time and the movement of said tag to a distance greater than said predetermined distance from said monitor.

18. A system as in claim 17 in which said monitor unit includes a transfer device for selectively transferring information regarding the support structure from whose monitor unit information is to be transferred to a different one of said support structures to facilitate maintenance of monitoring when a patient is transferred from one to another of said support structures, or where said monitoring is conducted by a monitor physically associated with the patient such that said monitor moves with said patient when said patient moves.

19. A system as in claim 13 including one or more of said monitor units at a hand washing station, and a hand washing detector for detecting a hand washing procedure by the carrier of said tag, and for energizing said indicator on said tag, said monitor units being associated with one another in a wireless network through which information is transmitted to said device for storage.

20. A system as in claim 12 in which said ranging signals comprise first and second wireless signals of different transmission velocities, said system including a device for measuring the difference between the time of flight of said wireless signals and determining when said difference falls below a predetermined minimum.

21. A system as in claim 12 in which said equipment in said monitor is adapted to transmit to said other device for storage information indicating that said indicator has been turned off, and the time of that occurrence.

22. A system as in claim 12 in which each of said monitor broadcasts its unique identification signal, and each of said tags stores that signal, compares it with a prior signal received from another monitor, and turns off the indicator on said tag if the compared signals do not match.

23. A system as in claim 12 including a motion detector located adjacent each of said patient support structures for enabling said equipment for sending said ranging signals only when said motion detector detects motion by a person within an area adjacent said patient support structure.

24. A method as in claim 23 including the step of holding said indicator in an activated condition while said wearer is in said near vicinity of said patient.

25. A system according to claim 1 for locating personnel in an enclosed facility having a plurality of spaced-apart stations, wherein said enclosed facility is a healthcare comprising;
   (a) a plurality of monitor units, each mounted on or near one of a plurality of stations in said facility;
   (b) a plurality of tags each carried by one of the personnel present in said facility, each of said tags being responsive to wireless signals from one of said monitor units to transmit identification signals identifying one of said personnel associated with said tag,
   (c) each of said monitor units having equipment for sending interrogation signals to said tags,
   (d) a motion detector responsive to the detection of the motion of a person adjacent said station; and
   (e) said monitor equipment being adapted to receive said identification signals from one of said tags which is determined to be within the range of said motion detector, and for transmitting a corresponding identification signal to another device for storage together with the time of detection.

26. A system as in claim 25 in which said tag includes an indicator for indicating the hand wash status of the carrier of said tag, and said tag includes a transmitter for transmitting to said monitor a signal indicating said hand wash status, and in which said equipment in said monitor is adapted to transmit a signal corresponding to said hand wash status signal to said other device for storage.

27. A system in claim 25 in which said equipment sends said interrogation signals repeatedly at timed intervals after being started by said motion detector and until no motion has been detected for a pre-determined length of time.

28. A method of locating personnel in an enclosed facility having a plurality of stations therein, the steps of
   (a) locating a detector at each of said stations for detecting the presence of a person when said person is within a predetermined distance from said detector by directing two signals of different velocities towards said person and measuring the time difference between the receipts of said signals by said person and comparing said difference with a predetermined value; and (b) developing and transmitting to said detector information identifying said person.

29. A method as in claim 28 including storing for each person detected the information received and the time when it is received.

30. A method as in claim 28 including locating a hand wash detector in at least some of said stations, said enclosed facility being one requiring frequent hand washing by personnel to retard the distribution of pathogens.

31. An identity and hand wash status badge to be displayed on healthcare personnel, said badge comprising (a) a display member; (b) a remotely actuatable visual hand wash status indicator on said display member; (c) a timing device for holding said indicator "on" for a first predetermined time period after being turned "on" and then turning said indicator "off" when said time period expires; and (d) said timing device being remotely actuatable to enable it to selectively hold said indicator "on" for a shorter length of time than said first time period said badge including a time-of-flight detector for detecting the difference in arrival times of two signals of different velocities sent from a measurement station and sending an identification signal when said difference is below a predetermined level.

32. A badge as in claim 16 including a vibrator for vibrating selectively when said indicator is "off".

33. An identity badge as in claim 31 including a wireless transceiver for transmitting badge identification and status indicator information in response to the receipt of signals from which the location of said badge within a predetermined distance from a monitor station can be determined.

34. An identity badge as in claim 33 in which said transceiver is adapted to transmit said information at different predetermined distances from said monitor station in response to the receipt of different wireless signals received from said monitor station.

35. A method of controlling an indicator on a tag worn by a healthcare worker in a healthcare facility comprising activating said indicator for a given time period after the completing of a hand washing procedure by said healthcare worker, and de-activating said indicator whenever said healthcare worker leaves the near vicinity of a patient in said facility, said tag worn by a healthcare worker including a time-of-flight detector for detecting the difference in arrival times of two signals of different velocities sent from a measurement station and sending an identification signal when said difference is below a predetermined level.

* * * * *